(12) United States Patent
Nawaz (10) Patent No.: US 10,246,386 B2
(45) Date of Patent: Apr. 2, 2019

(54) EMBEDDED ALKANE DEHYDROGENATION SYSTEMS AND PROCESSES

(71) Applicant: SABIC GLOBAL TECHNOLOGIES B.V., Bergen op Zoom (NL)

(72) Inventor: Zeeshan Nawaz, Riyadh (SA)

(73) Assignee: SABIC GLOBAL TECHNOLOGIES B.V., Bergen op Zoom (NL)

( * ) Notice: Subject to any disclaimer, the term of this patent is extended or adjusted under 35 U.S.C. 154(b) by 0 days.

(21) Appl. No.: 15/509,902

(22) PCT Filed: Sep. 9, 2015

(86) PCT No.: PCT/IB2015/056911
§ 371 (c)(1),
(2) Date: Mar. 9, 2017

(87) PCT Pub. No.: WO2016/038557
PCT Pub. Date: Mar. 17, 2016

(65) Prior Publication Data
US 2017/0297979 A1      Oct. 19, 2017

Related U.S. Application Data
(60) Provisional application No. 62/049,844, filed on Sep. 12, 2014.

(51) Int. Cl.
*B01J 8/06*     (2006.01)
*C07C 5/32*    (2006.01)
(Continued)

(52) U.S. Cl.
CPC .............. *C07C 5/3337* (2013.01); *B01J 8/062* (2013.01); *B01J 8/065* (2013.01); *B01J 8/067* (2013.01);
(Continued)

(58) Field of Classification Search
None
See application file for complete search history.

(56) References Cited

U.S. PATENT DOCUMENTS 2,304,203 A * 12/1942 Pyzel .................. B01J 8/062
196/134
2,399,678 A 5/1946 Houdry et al.
(Continued)

FOREIGN PATENT DOCUMENTS

| EP | 0298624 A2 * | 1/1989 | ............ B01J 8/062 |
| GB | 579102 A * | 7/1946 | ............ B01J 23/26 |

(Continued)

OTHER PUBLICATIONS

International Search Report for International Application PCT/IB2015/056911; dated Dec. 14, 2015; 5 pages.
(Continued)

Primary Examiner — Jennifer A Leung
(74) Attorney, Agent, or Firm — Cantor Colburn LLP (57) ABSTRACT

Systems for dehydrogenating an alkane are provided. An exemplary system includes a furnace and further includes alkane heating chambers, regeneration mixture heating chambers, and two groups of reaction chambers, all located within the furnace. The alkane heating chambers and regeneration mixture heating chambers can preheat an alkane feed and a regeneration mixture feed, respectively. The two groups of reaction chambers can be switchably coupled to an alkane feed and a regeneration mixture feed such that an alkane can flow through one group of reaction chambers while a regeneration mixture flows through the other group of reaction chambers. Processes for dehydrogenating an alkane are also provided.

19 Claims, 3 Drawing Sheets

(51) Int. Cl.
| | |
|---|---|
| *C07C 5/333* | (2006.01) |
| *C07C 5/48* | (2006.01) |
| *F27B 1/00* | (2006.01) |
| *F27B 1/08* | (2006.01) |
| *F27B 1/10* | (2006.01) |
| *F27D 99/00* | (2010.01) |
| *B01J 38/04* | (2006.01) |
| *B01J 38/06* | (2006.01) |
| *B01J 38/10* | (2006.01) |
| *B01J 38/12* | (2006.01) |
| *B01J 38/16* | (2006.01) |
| *B01J 38/38* | (2006.01) |
| *B01J 35/00* | (2006.01) |
| *B01J 23/26* | (2006.01) |
| *B01J 23/42* | (2006.01) |
| *B01J 23/62* | (2006.01) |
| *B01J 23/92* | (2006.01) |
| *B01J 23/96* | (2006.01) |
| *B01J 8/08* | (2006.01) |

(52) U.S. Cl.
CPC ............. *B01J 8/087* (2013.01); *B01J 23/26* (2013.01); *B01J 23/42* (2013.01); *B01J 23/626* (2013.01); *B01J 23/92* (2013.01); *B01J 23/96* (2013.01); *B01J 35/0006* (2013.01); *B01J 38/04* (2013.01); *B01J 38/06* (2013.01); *B01J 38/10* (2013.01); *B01J 38/12* (2013.01); *B01J 38/16* (2013.01); *B01J 38/38* (2013.01); *C07C 5/321* (2013.01); *C07C 5/3332* (2013.01); *C07C 5/3335* (2013.01); *C07C 5/48* (2013.01); *F27B 1/005* (2013.01); *F27B 1/08* (2013.01); *F27B 1/10* (2013.01); *F27D 99/0033* (2013.01); *B01J 2208/00194* (2013.01); *B01J 2208/06* (2013.01); *B01J 2208/065* (2013.01); *C07C 2523/26* (2013.01); *C07C 2523/42* (2013.01); *F23C 2900/05081* (2013.01); *Y02P 20/584* (2015.11)

(56) References Cited

U.S. PATENT DOCUMENTS

| | | | |
|---|---|---|---|
| 2,419,997 A | 5/1947 | Houdry | |
| 4,229,609 A * | 10/1980 | Hutson, Jr. | ............. B01J 23/96 585/660 |
| 4,560,824 A | 12/1985 | Spence et al. | |
| 4,581,339 A | 4/1986 | Bhatt et al. | |
| 4,746,643 A | 5/1988 | Buonomo et al. | |
| 4,996,387 A | 2/1991 | Gerhold et al. | |
| 5,866,745 A * | 2/1999 | Gartside | ................... C07C 4/06 208/130 |
| 6,191,332 B1 * | 2/2001 | Duee | ........................ B01J 8/062 422/109 |
| 6,326,523 B1 | 12/2001 | Stahl et al. | |
| 7,973,207 B2 | 7/2011 | Fridman et al. | |
| 8,188,328 B2 | 5/2012 | Fridman et al. | |
| 2010/0160705 A1 * | 6/2010 | Kosters | ................... B01J 8/062 585/654 |
| 2010/0233047 A1 | 9/2010 | Olbert et al. | |

FOREIGN PATENT DOCUMENTS

| | | |
|---|---|---|
| GB | 668280 A | 3/1952 |
| IT | 1242150 B | 2/1994 |
| WO | 2009003647 A1 | 1/2009 |
| WO | 2009003648 A1 | 1/2009 |

OTHER PUBLICATIONS

Italian Patent No. 1242150; Date of Publication: Feb. 16, 1994; Abstract Only, 1 page.
Written Opinion of the International Search Report for International Application PCT/IB2015/056911; dated Dec. 14, 2015; 6 pages.

* cited by examiner

EMBEDDED ALKANE DEHYDROGENATION SYSTEMS AND PROCESSES

CROSS REFERENCE TO RELATED APPLICATIONS

This application is a 371 of International Application No. PCT/IB2015/056911, filed Sep. 9, 2015, which claims priority to U.S. Application Ser. No. 62/049,844 filed Sep. 12, 2014, both of which are incorporated herein by reference on their entirety.

TECHNICAL FIELD

The presently disclosed subject matter relates to systems and processes for alkane dehydrogenation.

BACKGROUND

Alkane dehydrogenation can be a valuable process in which saturated hydrocarbons are converted to alkenes (olefins) and hydrogen ($H_2$). Examples of alkane dehydrogenation processes can include conversion of branched or unbranched $C_2$ to $C_{19}$ alkanes to the corresponding $C_2$ to $C_{19}$ alkenes, e.g., conversion of ethane to ethylene, propane to propylene, isobutane to isobutylene, and ethylbenzene to styrene. Alkane dehydrogenation reactions can be performed with heterogeneous catalysts.

Alkane dehydrogenation reactions can be performed with metal-based heterogeneous catalysts. The catalysts can contain metal oxides and/or elemental metal surfaces (active surfaces). The catalysts can be based on platinum (Pt) and other Group VIII metals. Other catalysts can include chromium (Cr) and/or chromium oxide. Additional heterogeneous catalysts for alkane dehydrogenation have also been reported. An alkane feed stream can be passed over or through the heterogeneous catalyst to produce a product stream containing an alkene and hydrogen. The heterogeneous catalyst can be positioned in a catalyst tube, catalyst bed, or catalyst-filled plate. Alkane dehydrogenation reactions are endothermic and can be conducted at a high temperature. For example, the alkane feed stream can be preheated to a temperature in the range of about 550° C. to about 700° C. and the reaction conducted within the same temperature range. At such high temperatures, side reactions can occur and coke (carbon residue) can form. Carbon deposition on the surface of heterogeneous catalysts can reduce catalytic activity. Thus, over time, conversion and efficiency of alkane dehydrogenation can decline if catalysts are not regenerated or replaced.

Choice of catalyst can influence the optimal parameters for alkane dehydrogenation. Certain Cr-based catalysts can be highly active and achieve high conversion of alkanes to alkenes but can be deactivated relatively quickly, which can require relatively frequent regeneration, e.g., after about 5 to 20 minutes of operation. Certain Pt-based catalysts can be less active than Cr-based catalysts but can have improved resistance to deactivation and can require relatively infrequent regeneration, e.g., after about 6 to 12 hours of operation.

Accordingly, alkane dehydrogenation catalysts can require periodic regeneration. Catalysts can be regenerated by oxidation (burning) of carbon residues and, if necessary, reduction of the catalyst to restore catalytic activity. For example, regeneration of Pt- or Cr-based alkane dehydrogenation catalysts can involve (1) purging with steam, (2) exposure to a regeneration mixture stream containing steam and oxygen (which can oxidize carbon residues), (3) reduction, and (4) evacuation. Catalyst regeneration can be conducted at high temperature and can in many instances be conducted within the same temperature range at which the alkane dehydrogenation reaction is conducted (e.g., about 550° C. to about 700° C.).

Certain techniques for alkane dehydrogenation can involve separate heating of (1) the alkane feed, (2) the dehydrogenation reaction catalyst tube(s), bed(s), or plate(s), and (3) the regeneration mixture feed. Separate heating of each component can be expensive due to high energy consumption and can also require complex reactor systems. Thus there remains a need for in the art for techniques for alkane dehydrogenation with reduced energy consumption and simplified operation.

SUMMARY

The presently disclosed subject matter provides systems and processes for dehydrogenating an alkane.

A system for dehydrogenating an alkane, comprising: a furnace; one or more alkane heating chambers located within the furnace for preheating an alkane feed; one or more regeneration mixture heating chambers located within the furnace for preheating a regeneration mixture feed; a first group of two or more reaction chambers located within the furnace for dehydrogenating an alkane, the first group of reaction chambers being switchably coupled to the alkane heating chambers to receive a heated alkane feed therefrom, and switchably coupled to the regeneration mixture heating chambers to receive a heated regeneration mixture feed therefrom; and a second group of two or more reaction chambers located within the furnace for dehydrogenating an alkane, the second group of reaction chambers being switchably coupled to the alkane heating chambers to receive a heated alkane feed therefrom, and switchably coupled to the regeneration mixture heating chambers and configured to receive a heated regeneration mixture feed therefrom; the system being configured such that when the first group of reaction chambers are switched to receive the heated alkane feed, the second group of reaction chambers are switched to receive the heated regeneration mixture feed; and when the first group of reaction chambers are switched to receive the heated regeneration mixture feed, the second group of reaction chambers are switched to receive the heated alkane feed.

A system for dehydrogenating an alkane, comprising: a furnace; means for alkane heating located within the furnace, means for regeneration mixture heating located within the furnace, a first group of reaction chambers located within the furnace, and a second group of reaction chambers located within the furnace; and means for switchably feeding a heated alkane feed and a heated regeneration mixture feed into the first group of reaction chambers and the second group of reaction chambers.

A process for dehydrogenating an alkane, comprising: passing an alkane through one or more alkane heating chambers located within a furnace to provide a heated alkane, in a reaction phase, passing the heated alkane through one or more reaction chambers located within the furnace to provide a dehydrogenated product; passing a regeneration mixture through one or more regeneration mixture heating chambers located within the furnace to provide a heated regeneration mixture; after the reaction phase, in a regeneration phase, passing the heated regeneration mixture through the reaction chambers, to thereby regenerate a catalyst within the reaction chambers.

BRIEF DESCRIPTION OF THE DRAWINGS

The following is a brief description of the drawings wherein like elements are numbered alike and which are presented for the purposes of illustrating the exemplary embodiments disclosed herein and not for the purposes of limiting the same.

In the drawings, the same numbers are used in different drawings to denote the same or similar structures or processes.

DETAILED DESCRIPTION

The present disclosure provides improved systems and processes for alkane dehydrogenation that involve embedding an alkane feed, a dehydrogenation catalyst, and a regeneration mixture feed within a single furnace.

In one embodiment, an exemplary system for dehydrogenating an alkane includes a furnace and one or more alkane heating chambers located within the furnace for preheating an alkane feed. The system further includes one or more regeneration mixture heating chambers, also located within the furnace, for preheating a regeneration mixture feed. The system can further include a first group of two or more reaction chambers, also located within the furnace, for dehydrogenating an alkane. The first group of reaction chambers can be switchably coupled to the alkane heating chambers to receive a heated alkane feed therefrom and can be further switchably coupled to the regeneration mixture heating chambers to receive a heated regeneration mixture therefrom. The system can further include a second group of two or more reaction chambers, also located within the furnace, for dehydrogenating an alkane The second group of reaction chambers can be switchably coupled to the alkane heating chambers to receive a heated alkane feed therefrom and can be further switchably coupled to the regeneration mixture heating chambers to receive a heated regeneration mixture therefrom. The system can be configured such that when the first group of reaction chambers is switched to receive the heated alkane feed, the second group of reaction chambers is switched to receive the heated regeneration mixture feed. The system can be configured such that when the first group of reaction chambers is switched to receive the heated regeneration mixture feed, the second group of reaction chambers is switched to receive the heated alkane feed.

In certain embodiments, the system can include a heated alkane outlet line coupled to the alkane heating chambers, for removing a heated alkane from the alkane heating chambers. A first heated alkane feed line can be coupled to the heated alkane outlet line and further coupled to the first group of reaction chambers, for feeding the heated alkane from the heated alkane outlet line to the first group of reaction chambers. The system can further include a second heated alkane feed line coupled to the heated alkane outlet line and further coupled to the second group of reaction chambers, for feeding the heated alkane from the heated alkane outlet line to the second group of reaction chambers. The first and second heated alkane feed lines can include valves.

In certain embodiments, the system can include a heated regeneration mixture outlet line coupled to the regeneration mixture heating chambers, for removing a heated regeneration mixture from the regeneration mixture heating chambers. A first heated regeneration mixture feed line can be coupled to the heated regeneration mixture outlet line and further coupled to the first group of reaction chambers, for feeding the heated regeneration mixture from the heated regeneration mixture outlet line to the first group of reaction chambers. The system can further include a second heated regeneration mixture feed line coupled to the heated regeneration mixture outlet line and further coupled to the second group of reaction chambers, for feeding the heated regeneration mixture from the heated regeneration mixture outlet line to the second group of reaction chambers. The first and second heated regeneration mixture feed lines can include valves.

In certain embodiments, the alkane heating chambers and the regeneration mixture heating chambers can be positioned near the top of the furnace. In certain embodiments, the alkane heating chambers and the regeneration mixture heating chambers can be positioned adjacent to one another. In certain embodiments, the first group of reaction chambers and the second group of reaction chambers can be positioned adjacent to one another. The alkane heating chambers and the regeneration mixture heating chambers can be positioned within the furnace above the first group of reaction chambers and above the second group of reaction chambers.

In certain embodiments, the reaction chambers can include a Pt- or Cr-based catalyst. The catalyst can include chromium oxide.

The disclosed subject matter also provides processes for dehydrogenating an alkane. An exemplary process includes passing an alkane through one or more alkane heating chambers located within a furnace to provide a heated alkane The process further includes a reaction phase involving passing the heated alkane through one or more reaction chambers located within the furnace to provide a dehydrogenated product. The process further includes passing a regeneration mixture through one or more regeneration mixture heating chambers located within the furnace to provide a heated regeneration mixture. The process can further include, after the reaction phase, a regeneration phase involving passing the heated regeneration mixture through the reaction chambers, to regenerate a catalyst within the reaction chambers.

In certain embodiments, the reaction chambers can include a first group of reaction chambers and a second group of reaction chambers. In certain embodiments, the first group of reaction chambers can receive a heated alkane feed when the second group of reaction chambers receives a heated regeneration mixture feed. In certain embodiments, the first group of reaction chambers can receive a heated regeneration mixture feed when the second group of reaction chambers receives a heated alkane feed.

In certain embodiments, the alkane heating chambers can be heated to an alkane heating temperature and the regeneration mixture heating chambers can be heated to a regeneration mixture heating temperature. The alkane heating temperature and the regeneration mixture heating temperature can be approximately equal. In certain embodiments, the temperatures of the reaction phase and the regeneration phase can be approximately equal. In certain embodiments, the furnace can supply a predetermined amount of heat to the alkane heating chambers, the regeneration mixture heating chambers, and the reaction chambers. The furnace can supply heat to the alkane heating chambers, the regeneration mixture heating chambers, and the reaction chambers by one or more of convective heating and radiant heating.

In certain embodiments, the reaction chambers can have a gas hourly space velocity (GHSV) of about 1 $h^{-1}$ to about 10,000 $h^{-1}$.

In certain embodiments, processes for dehydrogenating an alkane can be operated continuously.

Alkane feeds useful in alkane dehydrogenation can include both linear and branched alkanes. The alkane feeds can include both lower alkanes (i.e., alkanes having eight or fewer carbon atoms) and higher alkanes (i.e., alkanes have nine or more carbon atoms). Suitable alkane feeds can also include other compounds that contain saturated hydrocarbon moieties (e.g., a —$CH_2$—$CH_2$— moiety) capable of dehydrogenation to an alkene moiety. As used herein, the term "alkane feed" can encompass compounds that incorporate moieties other than saturated hydrocarbons, e.g., unsaturated hydrocarbon moieties and/or heteroatoms. For example, an alkane feed suitable for alkane dehydrogenation can include ethylbenzene. Ethylbenzene contains an unsaturated moiety, but it also contains an alkyl group (an ethyl group) that can undergo dehydrogenation to provide styrene. Other non-limiting examples of alkanes suitable for alkane dehydrogenation can include ethane, propane, n-butane, i-butane, n-pentane, i-pentane, neopentane, $C_6$-$C_{19}$ linear hydrocarbons, and $C_6$-$C_{19}$ branched hydrocarbons.

In certain embodiments, alkane feeds can include other components. For example, an alkane feed can include hydrogen ($H_2$). Hydrogen can be present as an impurity in a stream of alkane compounds, or hydrogen can be co-injected into an alkane feed stream. Hydrogen can help to reduce coke formation. Steam can also be co-injected into an alkane feed stream as a diluent. Steam can help to reduce coke formation. A diluent can help to maintain a positive pressure within the reactor or reaction chambers and can reduce the partial pressures of alkane compounds and hydrogen. A diluent (e.g., steam) can help to reduce coke formation and can improve catalyst lifetime and overall efficiency. An alkane feed can also include carbon monoxide (CO) and/or carbon dioxide ($CO_2$). CO and/or $CO_2$ can act as a fluffing gas. An alkane feed can include small amounts of sulfur compounds. For example, in certain embodiments the alkane feed can include sulfur compounds in an amount up to about 200 parts per million (ppm).

Alkane dehydrogenation reactions can be performed with metal-based heterogeneous catalysts. The catalysts can contain metal oxides and/or elemental metal surfaces. The catalysts can be based on platinum (Pt) or other Group VIII metals. Pt and other Group VIII metals can be useful in catalysis of alkane dehydrogenation, as Pt and other Group VIII metals can have high activity in activating C—H bonds. Catalysts based on Pt and other Group VIII metals can have high selectivity for activating C—H bonds over C—C bonds. Metallic Pt(0) surfaces can activate C—H bonds. Catalysts based on Pt and other Group VIII metals can also include other metals as well, e.g., Sn, In, Pb, Cu, Mn, Co, K, Na, and/or Ca.

Catalysts for alkane dehydrogenation can also be based on chromium (Cr) and/or chromium oxide. Chromium oxide can be Cr(III) oxide, i.e., $Cr_2O_3$. Chromium oxide is also known as chromia. Additional heterogeneous catalysts for alkane dehydrogenation can be used, e.g., zinc (Zn) titanates and sulfided nickel (Ni).

Catalysts for alkane dehydrogenation can be heterogeneous catalysts. The heterogeneous catalysts can include solid supports or solid carriers that increase the surface area of the catalyst. Examples of solid supports and solid carriers used to prepare heterogeneous catalysts can include various metal salts, metalloid oxides, and metal oxides, e.g., titania (titanium oxide), zirconia (zirconium oxide), silica (silicon oxide), alumina (aluminum oxide), magnesium oxide, and magnesium chloride.

In certain non-limiting embodiments, the catalyst can include $Cr_2O_3$ (chromium(III) oxide) on an alumina support. For example, the catalyst can be activated alumina impregnated with 17-23 weight % chromium, in the form of chromium oxide. In certain non-limiting embodiments, the catalyst can include Pt on an alumina support. For example, the catalyst can be a Pt—Sn mixture supported on alumina.

A heterogeneous catalyst can be positioned in a catalyst tube, catalyst bed, catalyst column, or catalyst-filled plate. For example, a heterogeneous catalyst can be positioned in a packed bed, and gaseous reactants can be passed through the bed. The packed beds can themselves be positioned within reaction chambers or reaction channels through which a gas feed flows.

The reaction chambers can be packed bed chambers or packed bed reactors filled with heterogeneous catalyst. The catalyst can be physically mixed or layered within the reaction chambers. The catalyst can be mixed or layered with inert material that does not include catalyst. For example, layers of heterogeneous catalyst in a catalyst bed can be layered between a coarse inert material, which can improve flow distribution and/or bed mobility.

The reaction chambers can include one or more types of catalyst. For example, the reaction chambers can include multiple catalysts based on two or more different metals.

The reaction chambers can be tubular. The dimensions and scale of the reaction chambers can be variable and can depend on the desired feed and scale. In certain embodiments, the reaction chambers can be tubular and can have a width (diameter) in a range from about 0.05 centimeters (cm) to about 2 cm or more. In certain preferred embodiments, the reaction chambers can have a width in a range from about 0.2 cm to about 1 cm. Chambers of smaller diameter can have improved heat transfer properties but lower volume. The reaction chambers can have a gas hourly space velocity (GHSV) of about 1 $h^{-1}$ to about 10,000 $h^{-1}$. The optimal GHSV can vary depending on factors that include the type of catalyst used, the surface area and active metal loading of the catalyst, and the desired output of product. For example, the GHSV for a reaction chamber containing a Cr-based catalyst can be in a range from about 100 $h^{-1}$ to about 1,000 $h^{-1}$. The GHSV for a reaction chamber containing a Pt-based catalyst can be in a range from about 1 $h^{-1}$ to about 100 $h^{-1}$.

In certain embodiments, the reaction chambers can include a heat-generating component incorporated in the catalyst bed. The heat-generating component can be a component that generates a pre-determined amount of heat on exposure to reducing conditions and/or oxidizing conditions. The heat-generating component can help to establish and maintain an optimal temperature for alkane dehydrogenation and/or for catalyst regeneration within the reaction chambers. The heat-generating component can include a metal and a solid support. The metal in the heat-generating component can be selected from calcium aluminate, copper, chromium, molybdenum, vanadium, cerium, yttrium, scandium, tungsten, manganese, iron, cobalt, nickel, silver, bismuth, or a combination comprising at least one of the foregoing. The solid support in the heat-generating component can be selected from aluminum oxides, aluminum hydroxides, aluminum trihydroxide, boehmite, pseudoboehmite, gibbsite, bayerite, transition aluminas, alpha-alumina, gamma-alumina, silica/alumina, silica, silicates, aluminates, calcium aluminate, barium hexaluminate, calcined hydrotalcites, zeolites, zinc oxide, chromium oxides, magnesium oxides, or a combination comprising at least one of the foregoing.

As noted above, catalysts for alkane dehydrogenation can require periodic regeneration. Catalyst regeneration can involve (1) purging the reaction chambers and catalyst beds or catalyst plates, (2) exposing the catalyst to oxygen or a mixture of steam and oxygen, (3) reduction of the catalyst, and (4) evacuation of the reaction chambers. The purging step can involve purging with steam. In certain embodiments, the purging step can involve purging with an oxygen source, e.g., oxygen gas, air, steam, another oxygen source, or a mixture thereof. The oxygen source can be a mild oxygen source. Exposing the catalyst to oxygen or a mixture of steam and oxygen can oxidize (i.e., burn) coke residues (i.e., carbon residues) on the catalyst. The oxygen source can be air, or the oxygen source can be a more concentrated oxygen source. Removal of coke residues can restore catalytic activity by reestablishing active catalytic sites on the heterogeneous catalyst. In some instances, oxidation of coke residues can also cause oxidation of the catalyst. For example, if the catalyst is a Pt-based catalyst, exposure to oxygen at high temperature can cause oxidation of the Pt-based catalyst. Catalytic activity can be restored by reduction of the catalyst, e.g., regeneration of Pt centers. Reduction of the oxidized catalyst can be achieved with a reducing agent, e.g., hydrogen ($H_2$), methane, and/or an alkane compound.

As used herein, the term "regeneration mixture" can encompass a gas mixture that includes oxygen, air, steam, hydrocarbons, and/or fuel gas. The regeneration mixture can be steam alone, in the absence of oxygen, e.g., when steam is used as a purge gas. The regeneration mixture can also include hydrogen, methane, and/or other alkane compounds, e.g., when hydrogen, methane, and/or other alkane compounds are used as a reducing mixture. The composition of the regeneration mixture can vary during a regeneration process. For example, a regeneration mixture can initially include steam (e.g., in a purging step), then steam and oxygen (e.g., in an oxidation step), and then hydrogen and/or methane (e.g., in a reduction step). The term "regeneration mixture" is not limited to oxygen or oxygen/steam mixtures.

Figure 1:
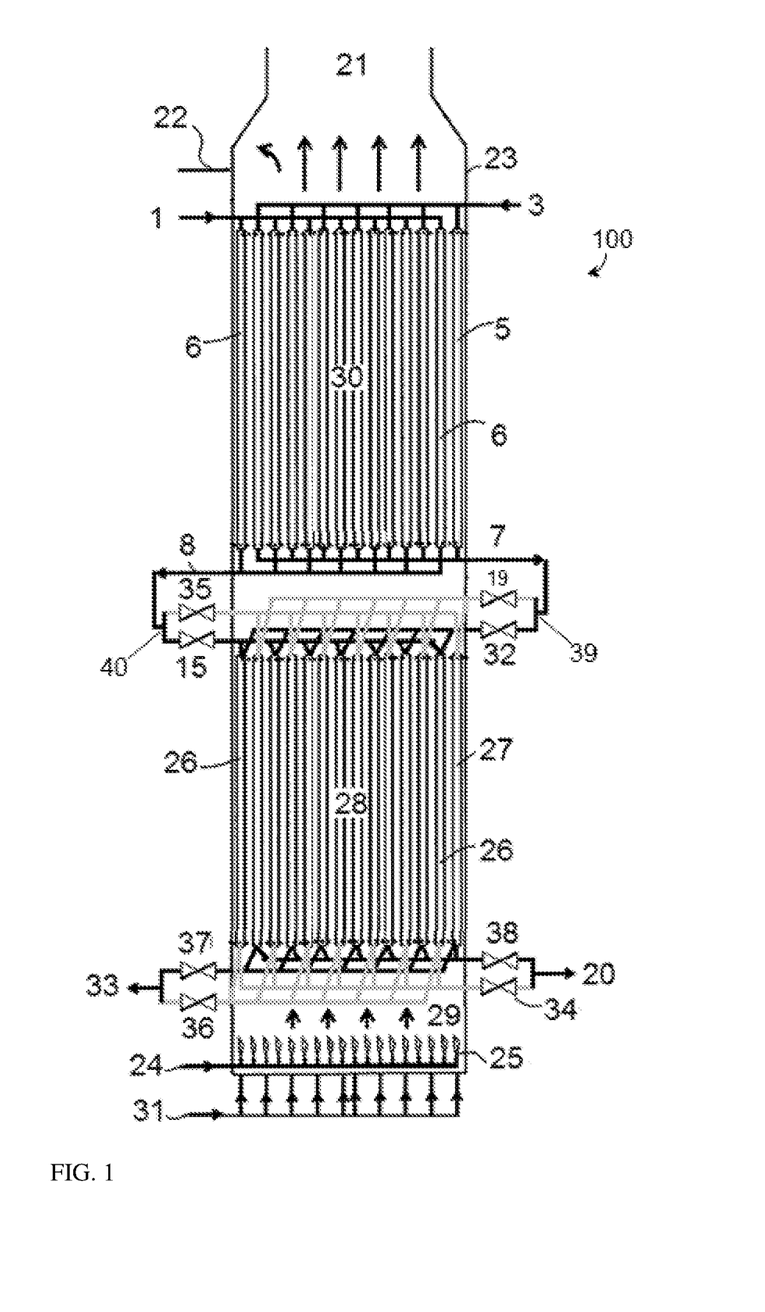
FIG. 1 is a schematic diagram showing an exemplary system for dehydrogenating an alkane, in accordance with one non-limiting embodiment of the disclosed subject matter.

For the purpose of illustration and not limitation, FIG. 1 is a schematic representation of an exemplary system according to the disclosed subject matter. The exemplary system 100 includes a furnace 23. The system 100 further includes one or more alkane heating chambers 6 located within the furnace 23. The system 100 can include multiple alkane heating chambers 6, e.g., two to five, five to ten, ten to fifty, fifty to one hundred, one hundred to five hundred, or five hundred to one thousand chambers. The alkane heating chambers 6 are coupled to an alkane feed line 1 and configured to receive an alkane feed from the alkane feed line 1. The alkane in the alkane heating chambers 6 is heated. The alkane heating chambers 6 are further coupled to a heated alkane outlet line 8, which is configured to receive a heated alkane feed from the alkane heating chambers 6. The heated alkane outlet line 8 can remove a heated alkane stream from alkane heating chambers 6.

In certain embodiments, the alkane feed line 1 can feed an alkane that is already warmed. For example, the alkane feed can have a temperature of about 150° C. to about 350° C. The alkane feed can be derived from a hydrocarbon stream and can be warmed in a gas-gas heat exchanger, which can be located outside of the furnace 23.

The system 100 further includes one or more regeneration mixture heating chambers 5 located within the furnace 23. The system 100 can include multiple regeneration mixture heating chambers 5, e.g., two to five, five to ten, ten to fifty, fifty to one hundred, one hundred to five hundred, or five hundred to one thousand chambers. The system 100 can include equal numbers of alkane heating chambers 6 and regeneration mixture heating chambers 5. The regeneration mixture heating chambers 5 can be coupled to a regeneration mixture feed line 3 and configured to receive a regeneration mixture feed from the regeneration mixture feed line 3. The regeneration mixture in the regeneration mixture heating chambers 5 is heated. The regeneration mixture heating chambers 5 are further coupled to a heated regeneration mixture outlet line 7, which is configured to receive a heated regeneration mixture from the regeneration mixture heating chambers 5. The heated regeneration mixture outlet line 7 can remove a heated regeneration mixture stream from regeneration mixture heating chambers 5.

The system 100 further includes a first group of two or more reaction chambers 26 located within the furnace 23. The individual reaction chambers within the first group 26 can be oriented parallel to one another. The system 100 can include multiple reaction chambers within the first group 26, e.g., two to five, five to ten, ten to fifty, fifty to one hundred, one hundred to five hundred, or five hundred to one thousand chambers. The first group of reaction chambers 26 includes a catalyst for dehydrogenating an alkane The first group of reaction chambers 26 is coupled to a first heated alkane feed line 15 and configured to receive a heated alkane feed. The first heated alkane feed line 15 is switchably coupled to the heated alkane outlet line 8 through a three-way junction 40. The first heated alkane feed line 15 includes a switchable valve that can be opened to allow a heated alkane feed to flow from the heated alkane outlet line 8 through the first heated alkane feed line 15 and into the first group of reaction chambers 26, or closed to block the flow.

As used herein, a "switchable valve" is a valve that controls the flow of an effluent and can either allow or block the flow of an effluent. The switchable valve can operate in a first mode by forming an open passageway to allow an effluent to flow through the valve, and the valve can operate in a second mode by closing the passageway to block the flow of the effluent through the valve.

As used herein, the term "switchably coupled" means coupled in such a way that a flow or feed can be switched on or off. For example, a chamber that is switchably coupled to a first feed is coupled in such a way that the feed can flow into the chamber or can alternatively be blocked from flowing into the chamber. A chamber that is switchably coupled to a first feed and further switchably coupled to a second feed can be coupled through switchable valves to each feed. In a first mode, the switchable valves can allow the first feed to flow into the chamber while the second feed is blocked and, in a second mode, the switchable valves can allow the second feed to flow into the chamber while the first feed is blocked.

The first group of reaction chambers 26 is also coupled to a first heated regeneration mixture feed line 32 and configured to receive a heated regeneration mixture feed. The first heated regeneration mixture feed line 32 is switchably coupled to the heated regeneration mixture outlet line 7 through a three-way junction 39. The first heated regeneration mixture feed line 32 includes a switchable valve that can be opened to allow a heated regeneration mixture feed to flow from the heated regeneration mixture outlet line 7 through the first heated regeneration mixture feed line 32 and into the first group of reaction chambers 26, or closed to block the flow.

The system 100 further includes a second group of two or more reaction chambers 27 located within the furnace 23. The individual reaction chambers within the second group 27 can be oriented parallel to one another. The second group of reaction chambers 27 includes a catalyst for dehydrogenating an alkane The second group of reaction chambers 27 is coupled to a second heated alkane feed line 35 and configured to receive a heated alkane feed. The second heated alkane feed line 35 is switchably coupled to the heated alkane outlet line 8 through the three-way junction 40. The second heated alkane feed line 35 includes a switchable valve that can be opened to allow a heated alkane feed to flow from the heated alkane outlet line 8 through the second heated alkane feed line 35 and into the second group of reaction chambers 27, or closed to block the flow.

The second group of reaction chambers 27 is also coupled to a second heated regeneration mixture feed line 19 and configured to receive a heated regeneration mixture feed. The second regeneration mixture feed line 19 is switchably coupled to the heated regeneration mixture outlet line 7 through the three-way junction 39. The second heated regeneration mixture feed line 19 includes a switchable valve that can be opened to allow a heated regeneration mixture feed to flow from the heated regeneration mixture outlet line 7 through the first second regeneration mixture feed line 19 and into the second group of reaction chambers 27 or closed the block the flow.

The reaction chambers 26, 27 can include catalyst positioned within the chambers in catalyst beds or catalyst-filled plates. The catalyst loading can be dependent on the volume and space velocity of the chambers 26, 27 as well as on the activity of the catalyst.

In certain embodiments, the system 100 can include alkane heating chambers 6, regeneration mixture heating chambers 5, and reaction chambers 26, 27 all of similar dimensions. The system 100 can include similar numbers of alkane heating chambers 6, regeneration mixture heating chambers 5, reaction chambers 26, and reaction chambers 27. In such embodiments, the flow rates of effluents through each group of chambers 5, 6, 26, 27 can be similar.

The switchable valves of the first heated alkane feed line 15, the first heated regeneration mixture feed line 32, the second heated alkane feed line 35, and the second heated regeneration mixture feed line 19 are configured such that a heated alkane feed can be fed into the first group of reaction chambers 26 while a heated regeneration mixture feed is fed into the second group of reaction chambers 27, e.g., by closing the valves of the first heated regeneration mixture feed line 32 and the second heated alkane feed line 35 while opening the valves of the first heated alkane feed line 15 and the second heated regeneration mixture feed line 19. The valves are switchable, such that a heated alkane feed can alternatively be fed into the second group of reaction chambers 27 while a heated regeneration mixture feed is fed into the first group of reaction chambers 26, e.g., by closing the valves of the second heated regeneration mixture feed line 19 and the first heated alkane feed line 15 while opening the valves of the second heated alkane feed line 35 and the first heated regeneration mixture feed line 32. By switching these valves, the operator of the system 100 can determine which of the first group of reaction chambers 26 and the second group of reaction chambers 27 is in alkane dehydrogenation mode and which is in regeneration mode. The first group of reaction chambers 26 can receive a heated alkane feed (alkane dehydrogenation mode) when the second group of reaction chambers 27 receives a heated regeneration mixture feed (regeneration mode), or vice versa.

The reaction chambers 26, 27 and the various lines 7, 8, 15, 19, 20, 32, 33, 34, 35, 36, 37, and 38 are configured such that the reaction chambers 26, 27 can be evacuated. The reaction chambers 26, 27 can be placed under vacuum (i.e., reduced pressure) to remove gas inside the chambers 26, 27. The pressures within the groups of reaction chambers 26, 27 can be reduced below atmospheric pressure, e.g., below about 100 kiloPascals (kPa) (below about 1 bar), below about 50 kPa (below about 0.5 bar), below about 10 kPa (below about 0.1 bar), or below about 1 kPa (below about 0.01 bar). Evacuation of the reaction chambers 26, 27 can be performed as the chambers are switched from regeneration mode to alkane dehydrogenation mode. In other words, regeneration mixture can be removed from the reaction chambers 26, 27 by evacuation before alkane is introduced to the reaction chambers 26, 27 when the chambers 26, 27 are switched from regeneration mode to alkane dehydrogenation mode.

As the first group of reaction chambers 26 receive an alkane feed and catalyze an alkane dehydrogenation reaction, the catalyst within the first group of reaction chambers 26 can gradually lose catalytic activity. When catalytic activity within the first group of reaction chambers 26 declines below a threshold, alkane feed can be diverted from the first group of reaction chambers 26 into the second group of reaction chambers 27, and regeneration mixture can be sent to the first group of reaction chambers 26 to regenerate the catalyst therein. The second group of reaction chambers 27 can then catalyze an alkane dehydrogenation reaction while catalyst in the first group of reaction chambers 26 is regenerated. When regeneration of the catalyst in the first group of reaction chambers 26 is complete and catalytic activity in the second group of reaction chambers 27 declines, alkane feed can be diverted from the second group of reaction chambers 27 and back to the first group of reaction chambers 26. In this way, the system 100 is designed such that it can continuously receive and process an alkane feed and catalyze an alkane dehydrogenation reaction. The system 100 can be operated in a continuous mode. While one group of reaction chambers 26 or 27 within the system 100 promotes alkane dehydrogenation, the other group of reaction chambers 26 or 27 is regenerated.

The system 100 can include a product outlet line 33 to remove a product stream from the first group of reaction chambers 26 and the second group of reaction chambers 27. The product outlet line 33 can remove products of alkane dehydrogenation (e.g., alkene compounds) from the reaction chambers. The product outlet line 33 can be coupled to the first group of reaction chambers 26 through an outlet line 36 for products from the first group of reaction chambers. The outlet line 36 for products from the first group of reaction chambers includes a switchable valve. The product outlet line 33 can be further coupled to the second group of reaction chambers 27 through an outlet line 37 for products from the second group of reaction chambers. The outlet line 37 for products from the second group of reaction chambers includes a switchable valve.

Thus when the first group of reaction chambers 26 are receiving an alkane feed and operating in alkane dehydrogenation mode and the second group of reaction chambers 27 is receiving a regeneration mixture feed and operating in regeneration mode, the valve of the outlet line 36 for products from the first group of reaction chambers can be opened while the valve of the outlet line 37 for products from the second group of reaction chambers is closed, such that products of alkane dehydrogenation flow from the first group of reaction chambers 26 through the outlet line 36 for products from the first group of reaction chambers and are removed by the product outlet line 33. When the second group of reaction chambers 27 are receiving an alkane feed and operating in alkane dehydrogenation mode and the first group of reaction chambers 26 is receiving a regeneration mixture feed and operating in regeneration mode, the valve of the outlet line 37 for products from the second group of reaction chambers can be opened while the valve of the outlet line 36 for products from the first group of reaction chambers is closed, such that products of alkane dehydrogenation flow from the second group of reaction chambers 27 through the outlet line 37 for products from the second group of reaction chambers and are removed by the product outlet line 33.

The system 100 can also include an outlet line 20 for effluents from regeneration to remove an effluent stream from the first group of reaction chambers 26 and the second group of reaction chambers 27. The outlet line 20 for effluents from regeneration can remove effluents from regeneration (e.g., oxygen, steam, hydrogen, carbon monoxide, and/or carbon dioxide) from the reaction chambers. The outlet line 20 for effluents from regeneration can be coupled to the first group of reaction chambers 26 through an outlet line 34 for effluents from regeneration of the first group of reaction chambers. The outlet line 34 for effluents from regeneration of the first group of reaction chambers includes a switchable valve. The outlet line 20 for effluents from regeneration can be further coupled to the second group of reaction chambers 27 through an outlet line 38 for effluents from regeneration of the second group of reaction chambers. The outlet line 38 for effluents from regeneration of the second group of reaction chambers also includes a switchable valve.

Thus when the first group of reaction chambers 26 are receiving an alkane feed and operating in alkane dehydrogenation mode and the second group of reaction chambers 27 are receiving a regeneration mixture feed and operating in regeneration mode, the valve of the outlet line 34 for effluents from regeneration of the first group of reaction chambers can be closed while the valve of the outlet line 38 for effluents from regeneration of the second group of reaction chambers is opened, such that effluents from regeneration flow from the second group of reaction chambers 27 through the outlet line 38 for effluents from regeneration of the second group of reaction chambers and are removed by the outlet line 20 for effluents from regeneration. When the second group of reaction chambers 27 are receiving an alkane feed and operating in alkane dehydrogenation mode and the first group of reaction chambers 26 is receiving a regeneration mixture feed and operating in regeneration mode, the valve of the outlet line 38 for effluents from regeneration of the second group of reaction chambers can be closed while the valve of the outlet line 34 for effluents from regeneration of the first group of reaction chambers is opened, such that effluents from regeneration flow from the first group of reaction chambers 26 through the outlet line 34 for effluents from regeneration of the first group of reaction chambers and are removed by the outlet line 20 for effluents from regeneration.

Products of alkane dehydrogenation (e.g., alkene compounds) can be recovered from the product outlet line 33. In certain embodiments, the product outlet line 33 can be further coupled to one or more gas-gas heat exchangers, where the stream of alkane dehydrogenation products can be used to heat another gas stream. For example, the stream of alkane dehydrogenation products can be used to heat the alkane feed 1. In certain embodiments, products of alkane dehydrogenation recovered from the product outlet line 33 can be purified to obtain pure products, e.g., pure alkene products. In certain embodiments, unreacted alkane can be recovered from the product outlet line 33. Unreacted alkane can be recycled back into the systems and processes of the present disclosure, e.g., by feeding through the alkane feed line 1. In certain embodiments, hydrogen can be recovered from the product outlet line 33.

Effluents from regeneration can be recovered from the outlet line 20 for effluents from regeneration. In certain embodiments, effluents from regeneration can include hydrogen, methane, and/or other hydrocarbon compounds. These compounds can be recovered and recycled into the system 100 or otherwise used. In certain embodiments, the effluents regeneration outlet line 20 can be further coupled to one or more gas-gas heat exchangers, where the stream of effluents from regeneration can be used to heat another gas stream.

The alkane heating chambers 6 and the regeneration mixture heating chambers 5 can be positioned together in a preheating zone 30. In the preheating zone 30, the alkane feed and the regeneration mixture feed can be heated. The alkane heating chambers 6 and the regeneration mixture heating chambers 5 can be positioned adjacent and parallel to one another, as depicted in FIG. 1. The alkane heating chambers 6 and the regeneration mixture heating chambers 5 can together be described as heating chambers or preheating chambers.

The first group of reaction chambers 26 and the second group of reaction chambers 27 can be positioned together in a reaction zone 28. The first group of reaction chambers 26 and the second group of reaction chambers 27 can be positioned adjacent and parallel to one another, as depicted in FIG. 1. The reaction zone 28 can be positioned within the furnace 23 below the preheating zone 30. The system 100 can include a stack of preheating chambers 5, 6 positioned above reaction chambers 26, 27. In certain embodiments, the preheating chambers 5, 6 can be positioned closer together, with less space between individual chambers, than the reaction chambers 26, 27.

The system 100 and furnace 23 enclose burners 25. The burners 25 are coupled to a fuel feed line 24, which is configured to feed a fuel to the burners 25. The burners 25 are further coupled to an air feed line 31, which is configured to feed air to the burners 25. The burners 25 combust a fuel and supply heat directly to the chamber of the furnace 25. The area of the burners 25 and immediately above the burners 25 can constitute a heating zone 29. Heat can rise from the heating zone 29 through first the reaction zone 28 and then the preheating zone 30. Exhaust gases rising through the furnace 23 can escape through an exhaust vent 21 at the top of the furnace. The furnace 23 heats the reaction zone 28 and preheating zone 30 and all components contained therein through both direct heating (radiant heating) as well as by convection. As shown in FIG. 1, the system 100 can be designed such that the temperature within the reaction chambers 26, 27 can be higher than the temperature within the alkane heating chambers 6 and the regeneration mixture heating chambers 5, due to the position of reaction chambers 26, 27 closer to the burners 25.

An area near the top of the furnace can be defined as the upper half of a vertically-oriented furnace, i.e., the area extending from the top of the furnace to a division halfway between the top of the furnace and the bottom of the furnace. By way of example, the area near the top of the furnace 23 shown in FIG. 1 can be defined as the area extending from the exhaust vent 21 to a division halfway between the exhaust vent 21 and the burners 25.

The alkane heating chambers 6 can be heated to an alkane heating temperature. The alkane heating temperature can be the temperature within the alkane heating chambers 6. The regeneration mixture heating chambers 5 can be heated to a regeneration mixture heating temperature. The regeneration mixture heating temperature can be the temperature within the regeneration mixture heating chambers 5. The alkane heating temperature and the regeneration mixture heating temperature can be approximately equal, e.g., within about 100° C. of each other.

The temperature of the first group of reaction chambers 26 and the second group of reaction chambers 27 can be set at an approximately constant value. The reaction chambers 26, 27 can be maintained at an approximately constant temperature while in both alkane dehydrogenation mode and regeneration mode. The temperature of the reaction chambers can be about 400° C. to about 900° C. In certain embodiments, the temperature of the reaction chambers can be 500° C. to about 750° C., e.g., at about 500° C., about 550° C., about 600° C., about 650° C., about 700° C., or about 750° C. At the temperatures described herein, both alkane dehydrogenation and catalyst regeneration can be carried out. In processes for dehydrogenating an alkane and regenerating a catalyst, the temperatures of the reaction phase and the regeneration phase can be approximately equal.

Temperatures that are "approximately constant" or "approximately equal" can be temperatures within a narrow range, e.g., within about 100° C.

To achieve an approximately constant temperature value in the reaction chambers 26, 27, the furnace 23, burners 25, fuel feed line 24, and air feed line 31 can be adjusted to provide a suitable, predetermined amount of heat to the reaction chambers 26, 27. In addition, as noted above, in certain embodiments the reaction chambers 26, 27 can include a heat-generating component, which can also supply heat to the reaction chambers 26, 27 when the reaction chambers 26, 27 are in alkane dehydrogenation and/or regeneration mode.

In certain embodiments, the pressure within the reaction chambers 26, 27 can be about 10 kPa to about 300 kPa (about 0.1 bar to about 3.0 bar) when the chambers 26, 27 are in alkane dehydrogenation mode.

In the exemplary system 100 shown in FIG. 1, the alkane heating chambers 6 and the regeneration mixture heating chambers 5 are separate and distinct. In the exemplary system 100, there are no switch valves within the reaction chambers 26, 27 themselves.

In certain embodiment, the preheating chambers 5, 6 can be tubular. The dimensions and scale of the preheating chambers 5, 6 can be variable and can depend on the desired feed and scale. In certain embodiments, the preheating chambers 5, 6 can be tubular and can have a width (diameter) in a range from about 1 cm to about 3 cm. Tubes of smaller diameter have improved heat transfer properties but lower volume.

The preheating chambers 5, 6 and the reaction chambers 26, 27 can be of various shapes known in the art. For example, the chambers 5, 6, 26, 27 can be U-shaped and/or straight.

The system 100 can include a thermocouple 22 for measuring the temperature of exhaust gas.

In certain embodiments, the alkane feed line 1 can feed propane to the system 100, and the product outlet line 33 can remove propylene (propene) from the system 100. In certain embodiments, the alkane feed line 1 can feed isobutane to the system 100, and the product outlet line 33 can remove isobutylene (isobutene) from the system 100.

Although the exemplary system 100 of FIG. 1 depicts a total of eight switchable valves on lines 15, 19, 32, 34, 35, 36, 37, and 38, it should be understood that FIG. 1 is a simplified, non-limiting representation, and the processes and systems of the present disclosure encompass other configurations. For example, switchable valves can be mounted at the inlet and/or outlet of each reaction chamber 26, 27 such that flows into each chamber can be individually controlled.

Figure 2:
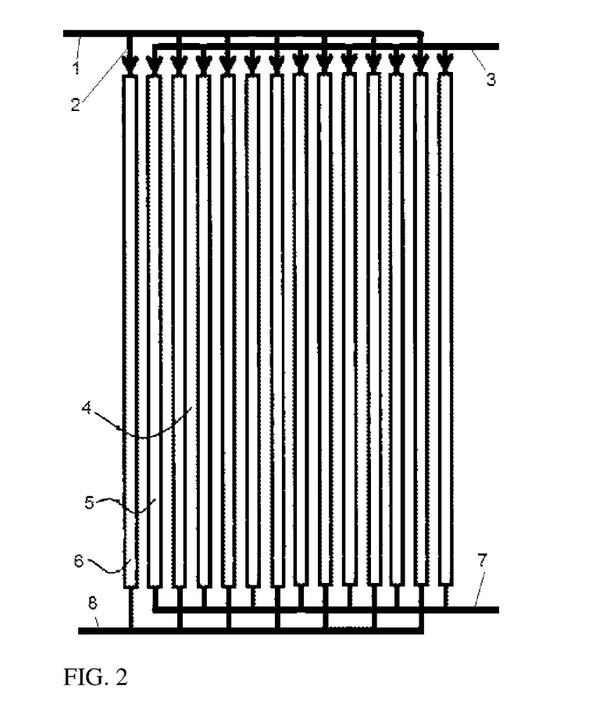
FIG. 2 is another schematic diagram showing an exemplary system for dehydrogenating an alkane, in accordance with one non-limiting embodiment of the disclosed subject matter.

For the purpose of illustration and not limitation, FIG. 2 is a schematic representation an exemplary system according to the disclosed subject matter. FIG. 2 shows alkane heating chambers 6 and regeneration mixture heating chambers 5. The alkane heating chambers 6 are coupled to an alkane feed line 1 and further coupled to a heated alkane outlet line 8. The alkane heating chambers 6 can be coupled to the alkane feed line 1 through sub-lines 2. The regeneration mixture heating chambers 5 are coupled to a regeneration mixture feed line 3 and further coupled to a heated regeneration mixture outlet line 7. The regeneration mixture heating chambers 5 can be coupled to the regeneration mixture feed line 3 through sub-lines. The alkane heating chambers 6 and regeneration mixture heating chambers 5 can be heated by hot gas passing through the spaces 4 between the chambers 5, 6.

Figure 3:
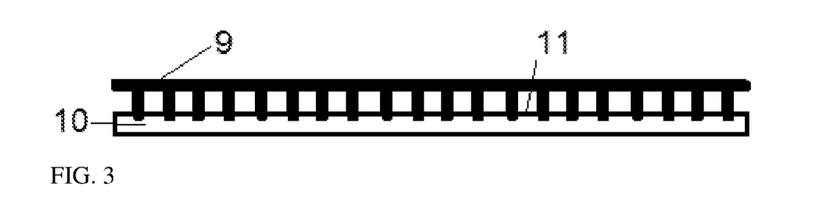
FIG. 3 is another schematic diagram showing an exemplary system for dehydrogenating an alkane, in accordance with one non-limiting embodiment of the disclosed subject matter.

For the purpose of illustration and not limitation, FIG. 3 is a schematic representation an exemplary system according to the disclosed subject matter. FIG. 3 shows that a feed line (e.g., an alkane feed line 1 or a regeneration mixture feed line 3) can be coupled to a sub-line 9, which can be further coupled to an individual chamber 10 (e.g., an alkane heating chamber 6 or a regeneration mixture heating chamber 5) through smaller pipes 11.

Figure 4:
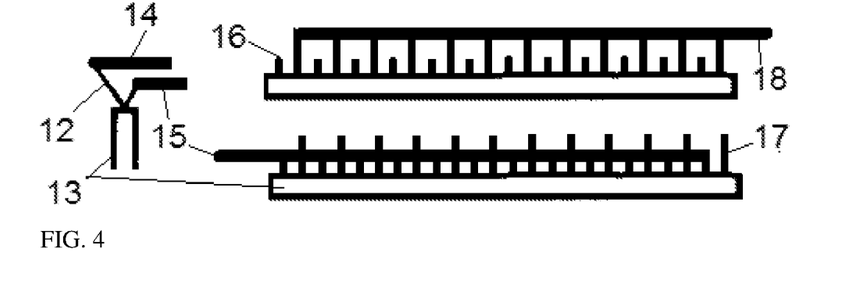
FIG. 4 is another schematic diagram showing an exemplary system for dehydrogenating an alkane, in accordance with one non-limiting embodiment of the disclosed subject matter.

For the purpose of illustration and not limitation, FIG. 4 is a schematic representation an exemplary system according to the disclosed subject matter. FIG. 4 demonstrates an embodiment where two channels are used at one time (as shown in FIG. 3) and are further connected to two inlets. One of these inlets contains pre-heated feed and the other inlet contains a pre-heated regeneration mixture. FIG. 4 depicts the upper portion of the reaction chambers 26, 27 that is not shown in FIG. 1. FIG. 4 shows heated alkane feed lines 14, 18 and heated regeneration mixture feed line 15 coupled to a reaction chamber 13. Feed lines 14, 15, 18 can be coupled to reaction chambers through smaller connective lines 12, 16, 17.

Figure 5:
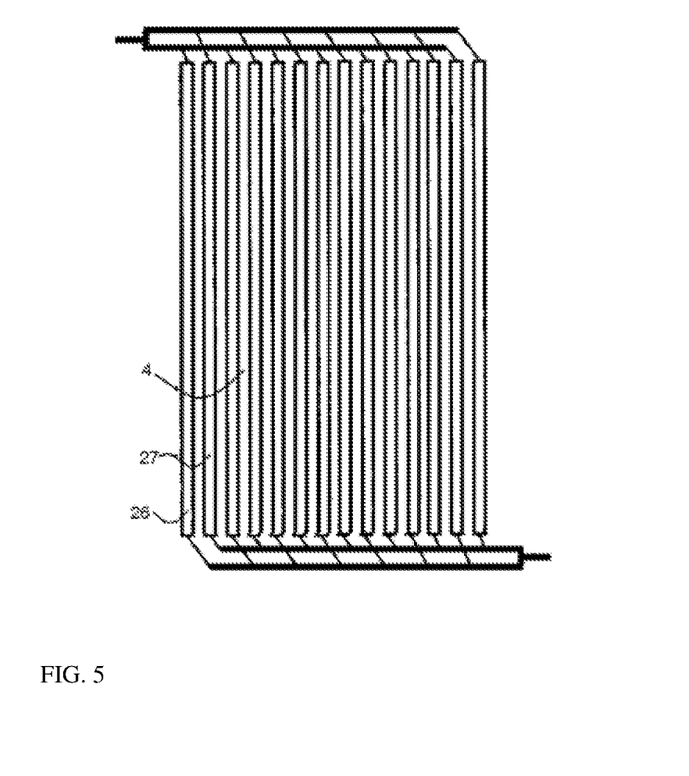
FIG. 5 is another schematic diagram showing an exemplary system for dehydrogenating an alkane, in accordance with one non-limiting embodiment of the disclosed subject matter.

For the purpose of illustration and not limitation, FIG. 5 is a schematic representation an exemplary system according to the disclosed subject matter. FIG. 5 shows a first group of reaction chambers 26 and a second group of reaction chambers 27. The chambers 26, 27 can be heated by hot gas passing through the spaces 4 between the chambers 26, 27. FIG. 5 further shows that the first group of reaction chambers 26 and the second group of reaction chambers 27 can be switched or alternated, such that one feed (e.g., a reaction feed) flows through one group while a second feed (e.g., a regeneration feed) flows through the second group.

The dimensions of the chambers and lines of the exemplary system 100 are not fixed and can be adjusted according to the desired scale and production capacity of the system 100.

In one embodiment, an exemplary process for dehydrogenating an alkane includes passing an alkane through one or more alkane heating chambers to provide a heated alkane With reference to FIG. 1 described above, the process can include feeding an alkane from an alkane feed line 1 into one or more alkane heating chambers 6. The alkane passes through the alkane heating chambers 6 to provide a heated alkane. The heated alkane can be removed from the alkane heating chambers 6 through a heated alkane outlet line 8. Depending on which of the valves of the first heated alkane feed line 15 and the second heated alkane feed line 35 is open and which is closed, the heated alkane can pass into and through either a first group of reaction chambers 26 or a second group of reaction chambers 27. As the heated alkane passes through the reaction chambers 26 or 27, catalyst within the reaction chambers promotes a dehydrogenation reaction of the alkane to provide a dehydrogenated product (e.g., an alkene). This phase of the process can be described as a reaction phase. The product can then be removed from the reaction chambers 26 or 27 through a product outlet line 33.

The exemplary process further includes passing a regeneration mixture through one or more regeneration mixture heating chambers to provide a heated regeneration mixture. The process can include feeding a regeneration mixture from a regeneration mixture feed line 3 into one or more regeneration mixture heating chambers 5. The regeneration mixture passes through the regeneration mixture heating chambers 5 to provide a heated regeneration mixture. The heated regeneration mixture can be removed from the regeneration mixture heating chambers 5 through a heated regeneration mixture outlet line 7. Depending on which of the valves of the first heated regeneration mixture feed line 32 and the second heated regeneration mixture feed line 19 is open and which is closed, the heated regeneration mixture can pass into and through either the first group of reaction chambers 26 or the second group of reaction chambers 27. As the heated regeneration mixture passes through the reaction chambers 26 or 27, catalyst within the reaction chambers can be regenerated.

In certain embodiments, the process can include changing the composition of the heated regeneration mixture as it passes through the reaction chambers 26 or 27. For example, the process can include first passing heated steam through the reaction chambers 26 or 27, followed by passing oxygen and steam, followed by passing a reducing agent, followed by evacuation of the reaction chambers 26 or 27. The regeneration mixture can then be removed from the reaction chambers 26 or 27 through an effluent from regeneration outlet line 20. Regeneration can occur after the reaction phase.

In the processes and systems of the present disclosure, conversion of saturated hydrocarbons (e.g., ethane, propane, and isobutane) to the corresponding alkenes can, in certain embodiments, vary in a range from about 20% to about 65%. The yield per cycle of alkane dehydrogenation can be greater than 20%. The reaction selectivity for the desired alkene product over other products can vary in a range from about 50% to about 98%.

The length of time required for catalyst regeneration can depend on many variables, including, for example, the type of catalyst used, the scale of the catalyst beds or plates, the composition of the regeneration mixture, and the temperature of the regeneration mixture. In certain embodiments, the length of time for regeneration of Cr-based catalysts can be in a range from about 5 minutes to about 30 minutes. During this length of time, the Cr-based catalysts can be regenerated by purging, regeneration, reduction, and evacuation. In certain embodiments, the length of time for regeneration of Pt-based catalysts can be in a range from about 1 hour to about 10 hours. During this length of time, the Pt-based catalysts can be regenerated by purging, regeneration, reduction, and evacuation. During the time that one group of reaction chambers 26 or 27 are being regenerated, alkane dehydrogenation can be conducted in the other group of reaction chambers 26 or 27.

Regeneration of Pt-based catalysts can include redispersion of active metal. For example, a mild chlorine reagent can be injected into reaction chambers 26 and/or 27 to redisperse active Pt.

In certain embodiments, the systems and processes of the present disclosure can be adapted for oxidative dehydrogenation of an alkane. In oxidative dehydrogenation of an alkane, as distinct from standard dehydrogenation of an alkane, alkane compounds are converted to alkene compounds in the presence of oxygen ($O_2$), and water ($H_2O$) rather than hydrogen ($H_2$) is formed as a byproduct. Oxidative dehydrogenation is an exothermic process rather than endothermic. Accordingly, oxidative dehydrogenation does not require input of heat to proceed, as standard dehydrogenation does. The systems and processes of the present disclosure can be adapted for oxidative dehydrogenation with minor adjustments. For example, oxygen gas can be co-injected with an alkane feed, and the temperature within the furnace can be reduced.

The processes and systems of the presently disclosed subject matter can have numerous advantages over existing technology, including prolonged catalyst life, reduced overall energy consumption, improved heat and mass transfer, improved control of temperature and product profile, reduced downtime, and simplified operation. The systems for dehydrogenating an alkane of the present disclosure do not require a separate catalyst transfer line from a regenerator to a reactor.

The systems and processes disclosed herein include at least the following embodiments:

Embodiment 1: A system for dehydrogenating an alkane, comprising: a furnace; one or more alkane heating chambers located within the furnace for preheating an alkane feed; one or more regeneration mixture heating chambers located within the furnace for preheating a regeneration mixture feed; a first group of two or more reaction chambers located within the furnace for dehydrogenating an alkane, the first group of reaction chambers being switchably coupled to the alkane heating chambers to receive a heated alkane feed therefrom, and switchably coupled to the regeneration mixture heating chambers to receive a heated regeneration mixture feed therefrom; and a second group of two or more reaction chambers located within the furnace for dehydrogenating an alkane, the second group of reaction chambers being switchably coupled to the alkane heating chambers to receive a heated alkane feed therefrom, and switchably coupled to the regeneration mixture heating chambers and configured to receive a heated regeneration mixture feed therefrom; the system being configured such that when the first group of reaction chambers are switched to receive the heated alkane feed, the second group of reaction chambers are switched to receive the heated regeneration mixture feed; and when the first group of reaction chambers are switched to receive the heated regeneration mixture feed, the second group of reaction chambers are switched to receive the heated alkane feed.

Embodiment 2: The system of Embodiment 1, further comprising: a heated alkane outlet line coupled to the alkane heating chambers, for removing a heated alkane from the alkane heating chambers; a first heated alkane feed line coupled to the heated alkane outlet line and further coupled to the first group of reaction chambers, for feeding the heated alkane from the heated alkane outlet line to the first group of reaction chambers, the first heated alkane feed line comprising a valve; and a second heated alkane feed line coupled to the heated alkane outlet line and further coupled to the second group of reaction chambers, for feeding the heated alkane from the heated alkane outlet line to the second group of reaction chambers, the second heated alkane feed line comprising a valve.

Embodiment 3: The system of Embodiment 1 or Embodiment 2, further comprising: a heated regeneration mixture outlet line coupled to the regeneration mixture heating chambers, for removing a heated regeneration mixture from the regeneration mixture heating chambers; a first heated regeneration mixture feed line coupled to the heated regeneration mixture outlet line and further coupled to the first group of reaction chambers, for feeding the heated regeneration mixture from the heated regeneration mixture outlet line to the first group of reaction chambers, the first heated regeneration mixture feed line comprising a valve; and a second heated regeneration mixture feed line coupled to the heated regeneration mixture outlet line and further coupled to the second group of reaction chambers, for feeding the heated regeneration mixture from the heated regeneration mixture outlet line to the second group of reaction chambers, the second heated regeneration mixture feed line comprising a valve.

Embodiment 4: The system of any of the preceding Embodiments, wherein the alkane heating chambers and the regeneration mixture heating chambers are positioned near the top of the furnace.

Embodiment 5: The system of any of the preceding Embodiments, wherein the alkane heating chambers and the regeneration mixture heating chambers are positioned adjacent to one another.

Embodiment 6: The system of any of the preceding Embodiments, wherein the first group of reaction chambers and the second group of reaction chambers are positioned adjacent to one another.

Embodiment 7: The system as in either Embodiment 5 or Embodiment 6, wherein the alkane heating chambers and the regeneration mixture heating chambers are positioned within the furnace above the first group of reaction chambers and above the second group of reaction chambers.

Embodiment 8: The system of any of the preceding Embodiments, wherein the first group of reaction chambers and the second group of reaction chambers comprise a Pt- or Cr-based catalyst.

Embodiment 9: The system of Embodiment 8, wherein the catalyst comprises chromium oxide.

Embodiment 10: A system for dehydrogenating an alkane, comprising: a furnace; means for alkane heating located within the furnace, means for regeneration mixture heating located within the furnace, a first group of reaction chambers located within the furnace, and a second group of reaction chambers located within the furnace; and means for switchably feeding a heated alkane feed and a heated regeneration mixture feed into the first group of reaction chambers and the second group of reaction chambers.

Embodiment 11: The system of Embodiment 10, wherein the system is configured such that a heated alkane feed is fed into the first group of reaction chambers when a heated regeneration mixture feed is fed into the second group of reaction chambers and a heated regeneration mixture feed is fed into the first group of reaction chambers when a heated alkane feed is fed into the second group of reaction chambers.

Embodiment 12: A process for dehydrogenating an alkane, comprising: passing an alkane through one or more alkane heating chambers located within a furnace to provide a heated alkane, in a reaction phase, passing the heated alkane through one or more reaction chambers located within the furnace to provide a dehydrogenated product; passing a regeneration mixture through one or more regeneration mixture heating chambers located within the furnace to provide a heated regeneration mixture; after the reaction phase, in a regeneration phase, passing the heated regeneration mixture through the reaction chambers, to thereby regenerate a catalyst within the reaction chambers.

Embodiment 13: The process of Embodiment 12, wherein the reaction chambers comprise a Pt- or Cr-based catalyst.

Embodiment 14: The process of Embodiment 12 or Embodiment 13, wherein the reaction chambers comprise a first group of reaction chambers and a second group of reaction chambers, and the first group of reaction chambers receive a heated alkane feed when the second group of reaction chambers receive a heated regeneration mixture feed.

Embodiment 15: The process of any of Embodiments 12-14, wherein the reaction chambers comprise a first group of reaction chambers and a second group of reaction chambers and the first group of reaction chambers receive a heated regeneration mixture feed when the second group of reaction chambers receive a heated alkane feed.

Embodiment 16: The process of any of Embodiments 12-15, wherein the alkane heating chambers are heated to an alkane heating temperature, the regeneration mixture heating chambers are heated to a regeneration mixture heating temperature, and wherein the alkane heating temperature and the regeneration mixture heating temperature are approximately equal.

Embodiment 17: The process of any of Embodiments 12-16, whereby the furnace supplies a predetermined amount of heat to the alkane heating chambers, the regeneration mixture heating chambers, and the reaction chambers.

Embodiment 18: The process of either Embodiment 16 or Embodiment 17, whereby the furnace supplies heat to the alkane heating chambers, the regeneration mixture heating chambers, and the reaction chambers by one or more of convective heating and radiant heating.

Embodiment 19: The process of any of Embodiments 12-18, wherein the reaction chambers have a gas hourly space velocity (GHSV) of about 1 h$^{-1}$ to about 10,000 h$^{-1}$.

Embodiment 20: The process of any of Embodiments 12-19, whereby the process is operated continuously.

As used herein, the term "about" or "approximately" means within an acceptable error range for the particular value as determined by one of ordinary skill in the art, which will depend in part on how the value is measured or determined, i.e., the limitations of the measurement system. For example, "about" can mean a range of up to 20%, up to 10%, up to 5%, and or up to 1% of a given value.

In general, the invention may alternately comprise, consist of, or consist essentially of, any appropriate components herein disclosed. The invention may additionally, or alternatively, be formulated so as to be devoid, or substantially free, of any components, materials, ingredients, adjuvants or species used in the prior art compositions or that are otherwise not necessary to the achievement of the function and/or objectives of the present invention. The endpoints of all ranges directed to the same component or property are inclusive and independently combinable (e.g., ranges of "less than or equal to 25 wt %, or 5 wt % to 20 wt %," is inclusive of the endpoints and all intermediate values of the ranges of "5 wt % to 25 wt %," etc.). Disclosure of a narrower range or more specific group in addition to a broader range is not a disclaimer of the broader range or larger group. "Combination" is inclusive of blends, mixtures, alloys, reaction products, and the like. Furthermore, the terms "first," "second," and the like, herein do not denote any order, quantity, or importance, but rather are used to denote one element from another. The terms "a" and "an" and "the" herein do not denote a limitation of quantity, and are to be construed to cover both the singular and the plural, unless otherwise indicated herein or clearly contradicted by context. "Or" means "and/or." The suffix "(s)" as used herein is intended to include both the singular and the plural of the term that it modifies, thereby including one or more of that term (e.g., the film(s) includes one or more films). Reference throughout the specification to "one embodiment", "another embodiment", "an embodiment", and so forth, means that a particular element (e.g., feature, structure, and/or characteristic) described in connection with the embodiment is included in at least one embodiment described herein, and may or may not be present in other embodiments. In addition, it is to be understood that the described elements may be combined in any suitable manner in the various embodiments.

The modifier "about" used in connection with a quantity is inclusive of the stated value and has the meaning dictated by the context (e.g., includes the degree of error associated with measurement of the particular quantity). The notation "±10%" means that the indicated measurement can be from an amount that is minus 10% to an amount that is plus 10% of the stated value. The terms "front", "back", "bottom", and/or "top" are used herein, unless otherwise noted, merely for convenience of description, and are not limited to any one position or spatial orientation. "Optional" or "optionally" means that the subsequently described event or circumstance can or cannot occur, and that the description includes instances where the event occurs and instances where it does not. Unless defined otherwise, technical and scientific terms used herein have the same meaning as is commonly understood by one of skill in the art to which this invention belongs. A "combination" is inclusive of blends, mixtures, alloys, reaction products, and the like.

All cited patents, patent applications, and other references are incorporated herein by reference in their entirety. However, if a term in the present application contradicts or conflicts with a term in the incorporated reference, the term from the present application takes precedence over the conflicting term from the incorporated reference While particular embodiments have been described, alternatives, modifications, variations, improvements, and substantial equivalents that are or may be presently unforeseen may arise to applicants or others skilled in the art. Accordingly, the appended claims as filed and as they may be amended are intended to embrace all such alternatives, modifications variations, improvements, and substantial equivalents.

Although the presently disclosed subject matter and its advantages have been described in detail, it should be understood that various changes, substitutions and alterations can be made herein without departing from the spirit and scope of the disclosed subject matter as defined by the appended claims. Moreover, the scope of the disclosed subject matter is not intended to be limited to the particular embodiments described in the specification. Accordingly, the appended claims are intended to include within their scope such alternatives.

What is claimed is:

1. A system for dehydrogenating an alkane, comprising:
a furnace;
one or more alkane heating chambers located within the furnace for preheating an alkane feed;
one or more regeneration mixture heating chambers located within the furnace for preheating a regeneration mixture feed;
a first group of two or more reaction chambers located within the furnace for dehydrogenating an alkane, the first group of reaction chambers being switchably coupled to the one or more alkane heating chambers to receive a heated alkane feed therefrom, and switchably coupled to the one or more regeneration mixture heating chambers to receive a heated regeneration mixture feed therefrom; and
a second group of two or more reaction chambers located within the furnace for dehydrogenating an alkane, the second group of reaction chambers being switchably coupled to the one or more alkane heating chambers to receive a heated alkane feed therefrom, and switchably coupled to the one or more regeneration mixture heating chambers and configured to receive a heated regeneration mixture feed therefrom;
the system being configured such that when the first group of reaction chambers are switched to receive the heated alkane feed, the second group of reaction chambers are switched to receive the heated regeneration mixture feed; and
when the first group of reaction chambers is switched to receive the heated regeneration mixture feed, the second group of reaction chambers is switched to receive the heated alkane feed;
wherein the system further comprises a first heated alkane feed line coupled to a heated alkane outlet line and further coupled to the first group of reaction chambers, for feeding the heated alkane from the heated alkane outlet line to the first group of reaction chambers, the first heated alkane feed line comprising a first heated alkane feed line valve;
a second heated alkane feed line coupled to the heated alkane outlet line and further coupled to the second group of reaction chambers, for feeding the heated alkane from the heated alkane outlet line to the second group of reaction chambers, the second heated alkane feed line comprising a second heated alkane feed line valve;

a first heated regeneration mixture feed line coupled to a heated regeneration mixture outlet line and further coupled to the first group of reaction chambers, for feeding the heated regeneration mixture from the heated regeneration mixture outlet line to the first group of reaction chambers, the first heated regeneration mixture feed line comprising a first heated regeneration mixture feed line valve; and a second heated regeneration mixture feed line coupled to the heated regeneration mixture outlet line and further coupled to the second group of reaction chambers, for feeding the heated regeneration mixture from the heated regeneration mixture outlet line to the second group of reaction chambers, the second heated regeneration mixture feed line comprising a second heated regeneration mixture feed line valve;

wherein the first heated alkane feed line and the second heated alkane feed line each extend out of the furnace and each are separately directed back into the furnace after passing through the first heated alkane feed line valve and the second heated alkane feed line valve, respectively;

wherein the first heated regeneration mixture feed line and the second heated regeneration mixture feed line each extend out of the furnace and each separately are directed back into the furnace after passing through the first heated regeneration mixture feed line valve and the second heated regeneration mixture feed line valve, respectively;

where the first heated alkane feed line and the second heated alkane feed line are separate from one another and from the first heated regeneration mixture feed line and the second heated regeneration mixture feed line and wherein the first heated regeneration mixture feed line and the second heated regeneration mixture feed line are separate from one another and from the first heated alkane feed line and the second heated alkane feed line.

2. The system of claim 1, wherein
the heated alkane outlet line is coupled to the one or more alkane heating chambers, for removing the heated alkane from the one or more alkane heating chambers.

3. The system of claim 1, wherein
the heated regeneration mixture outlet line is coupled to the one or more regeneration mixture heating chambers, for removing the heated regeneration mixture from the one or more regeneration mixture heating chambers.

4. The system of claim 1, wherein the one or more alkane heating chambers and the one or more regeneration mixture heating chambers are positioned near the top of the furnace.

5. The system of claim 1, wherein the one or more alkane heating chambers and the one or more regeneration mixture heating chambers are positioned adjacent to one another.

6. The system of claim 1, wherein the first group of reaction chambers and the second group of reaction chambers are positioned adjacent to one another.

7. The system of claim 5, wherein the one or more alkane heating chambers and the one or more regeneration mixture heating chambers are positioned within the furnace above the first group of reaction chambers and above the second group of reaction chambers.

8. The system of claim 1, wherein the first group of reaction chambers and the second group of reaction chambers comprise a Pt- or Cr-based catalyst.

9. The system of claim 8, wherein the catalyst comprises chromium oxide.

10. The system of claim 1, wherein the first group of reaction chambers and the second group of reaction chambers comprise a catalyst-filled plate.

11. The system of claim 1, wherein an alkane heating temperature and a regeneration mixture heating temperature are within 100° C. of one another.

12. A system for dehydrogenating an alkane, comprising:
a furnace;
means for alkane heating located within the furnace, means for regeneration mixture heating located within the furnace, a first group of reaction chambers located within the furnace, and a second group of reaction chambers located within the furnace; and
means for switchably feeding a heated alkane feed and a heated regeneration mixture feed into the first group of reaction chambers and the second group of reaction chambers;
wherein the means for switchably feeding the heated alkane feed and the heated regeneration mixture feed comprises a first heated alkane feed line coupled to a heated alkane outlet line and further coupled to the first group of reaction chambers, for feeding the heated alkane from the heated alkane outlet line to the first group of reaction chambers, the first heated alkane feed line comprising a first heated alkane feed line valve;
a second heated alkane feed line coupled to the heated alkane outlet line and further coupled to the second group of reaction chambers, for feeding the heated alkane from the heated alkane outlet line to the second group of reaction chambers, the second heated alkane feed line comprising a second heated alkane feed line valve;
a first heated regeneration mixture feed line coupled to a heated regeneration mixture outlet line and further coupled to the first group of reaction chambers, for feeding the heated regeneration mixture from the heated regeneration mixture outlet line to the first group of reaction chambers, the first heated regeneration mixture feed line comprising a first heated regeneration mixture feed line valve; and
a second heated regeneration mixture feed line coupled to the heated regeneration mixture outlet line and further coupled to the second group of reaction chambers, for feeding the heated regeneration mixture from the heated regeneration mixture outlet line to the second group of reaction chambers, the second heated regeneration mixture feed line comprising a second heated regeneration mixture feed line valve;
wherein the first heated alkane feed line and the second heated alkane feed line each extend out of the furnace and each are separately directed back into the furnace after passing through the first heated alkane feed line valve and the second heated alkane feed line valve, respectively;
wherein the first heated regeneration mixture feed line and the second heated regeneration mixture feed line each extend out of the furnace and each separately are directed back into the furnace after passing through the first heated regeneration mixture feed line valve and the second heated regeneration mixture feed line valve, respectively;

where the first heated alkane feed line and the second heated alkane feed line are separate from one another and from the first heated regeneration mixture feed line and the second heated regeneration mixture feed line and wherein the first heated regeneration mixture feed line and the second heated regeneration mixture feed line are separate from one another and from the first heated alkane feed line and the second heated alkane feed line.

13. The system of claim 12, wherein the system is configured such that a heated alkane feed is fed into the first group of reaction chambers when a heated regeneration mixture feed is fed into the second group of reaction chambers and a heated regeneration mixture feed is fed into the first group of reaction chambers when a heated alkane feed is fed into the second group of reaction chambers.

14. A process for dehydrogenating an alkane, comprising:
passing an alkane through one or more alkane heating chambers located within a furnace to provide a heated alkane,
in a reaction phase, passing the heated alkane through one or more reaction chambers located within the furnace to provide a dehydrogenated product;
passing a regeneration mixture through one or more regeneration mixture heating chambers located within the furnace to provide a heated regeneration mixture;
after the reaction phase, in a regeneration phase, passing the heated regeneration mixture through the one or more reaction chambers, to thereby regenerate a catalyst within the one or more reaction chambers;
wherein the one or more reaction chambers comprise a first group of reaction chambers and a second group of reaction chambers, and the first group of reaction chambers receive a heated alkane feed when the second group of reaction chambers receive a heated regeneration mixture feed;
wherein the one or more alkane heating chambers are heated to an alkane heating temperature, the one or more regeneration mixture heating chambers are heated to a regeneration mixture heating temperature;
wherein a first heated alkane feed line is coupled to a heated alkane outlet line and further coupled to the first group of reaction chambers, for feeding the heated alkane from the heated alkane outlet line to the first group of reaction chambers, the first heated alkane feed line comprising a first heated alkane feed line valve;
a second heated alkane feed line is coupled to the heated alkane outlet line and further coupled to the second group of reaction chambers, for feeding the heated alkane from the heated alkane outlet line to the second group of reaction chambers, the second heated alkane feed line comprising a second heated alkane feed line valve;
a first heated regeneration mixture feed line is coupled to a heated regeneration mixture outlet line and further coupled to the first group of reaction chambers, for feeding the heated regeneration mixture from the heated regeneration mixture outlet line to the first group of reaction chambers, the first heated regeneration mixture feed line comprising a first heated regeneration mixture feed line valve; and
a second heated regeneration mixture feed line is coupled to the heated regeneration mixture outlet line and further coupled to the second group of reaction chambers, for feeding the heated regeneration mixture from the heated regeneration mixture outlet line to the second group of reaction chambers, the second heated regeneration mixture feed line comprising a second heated regeneration mixture feed line valve;
wherein the first heated alkane feed line and the second heated alkane feed line each extend out of the furnace and each are separately directed back into the furnace after passing through the first heated alkane feed line valve and the second heated alkane feed line valve, respectively;
wherein the first heated regeneration mixture feed line and the second heated regeneration mixture feed line each extend out of the furnace and each separately are directed back into the furnace after passing through the first heated regeneration mixture feed line valve and the second heated regeneration mixture feed line valve, respectively;
where the first heated alkane feed line and the second heated alkane feed line are separate from one another and from the first heated regeneration mixture feed line and the second heated regeneration mixture feed line and wherein the first heated regeneration mixture feed line and the second heated regeneration mixture feed line are separate from one another and from the first heated alkane feed line and the second heated alkane feed line.

15. The process of claim 14, wherein the the first group of reaction chambers receive a heated regeneration mixture feed when the second group of reaction chambers receive a heated alkane feed.

16. The process of claim 14, wherein the furnace supplies a predetermined amount of heat to the one or more alkane heating chambers, the one or more regeneration mixture heating chambers, and the one or more reaction chambers.

17. The process of Claim 14, wherein the furnace supplies heat to the one or more alkane heating chambers, the one or more regeneration mixture heating chambers, and the one or more reaction chambers by one or more of convective heating and radiant heating.

18. The process of claim 14, wherein the one or more reaction chambers have a gas hourly space velocity (GHSV) of about 1 $h^{-1}$ to about 10,000 $h^{-1}$.

19. The process of claim 14, wherein the process is operated continuously.

* * * * *